US007707736B2

(12) United States Patent
Keenan

(10) Patent No.: US 7,707,736 B2
(45) Date of Patent: May 4, 2010

(54) APPARATUS AND METHOD FOR OPTIMIZING A SURGICAL INCISION ON THE BREAST

(76) Inventor: Donald M. Keenan, 333 Fox Meadow Dr., Wexford, PA (US) 15090

( * ) Notice: Subject to any disclaimer, the term of this patent is extended or adjusted under 35 U.S.C. 154(b) by 762 days.

(21) Appl. No.: 11/605,035

(22) Filed: Nov. 28, 2006

(65) Prior Publication Data

US 2007/0141972 A1    Jun. 21, 2007

Related U.S. Application Data

(60) Provisional application No. 60/739,911, filed on Nov. 28, 2005.

(51) Int. Cl.
*B43L 13/20* (2006.01)
(52) U.S. Cl. ............................ 33/566; 33/512; 33/27.01
(58) Field of Classification Search ................ 33/27.01, 33/511, 512, 563, 565, 566, 613, 645
See application file for complete search history.

(56) References Cited

U.S. PATENT DOCUMENTS

| D167,043 | S | * | 6/1952 | Kintz | 33/563 |
|---|---|---|---|---|---|
| 4,389,782 | A | * | 6/1983 | Webster | 33/512 |
| 5,615,485 | A | * | 4/1997 | Stoneberg | 33/27.01 |
| 5,618,292 | A | * | 4/1997 | Poler | 33/512 |
| 6,216,354 | B1 | * | 4/2001 | Carbone | 33/565 |
| 6,321,457 | B1 | * | 11/2001 | Lariviere et al. | 33/563 |
| 6,981,988 | B1 | * | 1/2006 | Kinsley | 33/512 |
| 7,150,108 | B2 | * | 12/2006 | Babb | 33/563 |
| 2008/0125675 | A1 | * | 5/2008 | Lalonde | 600/587 |
| 2009/0204028 | A1 | * | 8/2009 | Richards | 600/587 |

* cited by examiner

*Primary Examiner*—G. Bradley Bennett
(74) *Attorney, Agent, or Firm*—The Webb Law Firm

(57) ABSTRACT

A device for establishing an area of incision on a breast includes a positioning component adapted to be positioned on or adjacent to a nipple areola complex of the breast and a template component connected to the positioning component. The template component includes at least one substantially arcuate-shaped stencil to facilitate a curved incision marking or curved incision on the breast. The device may include an elongated member connecting the template component to the positioning component. The template component may be pivotally attached to the elongated member and may be adjusted to move along the length of the elongated member. The positioning component may be substantially circular or substantially semi-circular. One or more handles may be attached to the device. A method for utilizing the aforementioned device is also disclosed.

10 Claims, 19 Drawing Sheets

APPARATUS AND METHOD FOR OPTIMIZING A SURGICAL INCISION ON THE BREAST

CROSS REFERENCE TO RELATED APPLICATIONS

This application claims the benefit of U.S. Provisional Patent Application No. 60/739,911 filed Nov. 28, 2005, and entitled "An Apparatus and Method for Optimizing a Surgical Incision on the Breast," the contents of which are incorporated herein by reference.

BACKGROUND OF THE INVENTION

1. Field of the Invention

The present invention relates to an apparatus and method for establishing an area of incision on a breast and, more particularly, to an apparatus conducive to creating an aesthetic incision on the breast with respect to skin lines thereof.

2. Description of Related Art

The precise position and shape of an incision for a breast operation facilitates the successful performance of the operation as well as the cosmetic appearance of the breast following surgery. Surgeons currently rely on visual or palpable reference points to place the incision in the desired location. Accordingly, the precision with which such a resultant incision is made varies which thereby may result in a less than optimal incision. It is therefore, desirable to overcome the above problem and others by increasing the precision of an incision made on the breast.

SUMMARY OF THE INVENTION

Accordingly, I have invented a device for establishing an area of incision on a breast. In a desirable embodiment, the device includes a positioning component and a template component. The positioning component is adapted to be positioned on or adjacent to a nipple areola complex ("NAC") of the breast. The template component is connected to the positioning component and includes at least one stencil shaped to facilitate a curved incision marking or curved incision on the breast. In one embodiment, the stencil includes an arc portion having a first and second end connected by a respective first and second radial support extending from the positioning component. The positioning component may be substantially circular or substantially semi-circular. The substantially circular positioning component may be sized to substantially matingly receive the nipple of the NAC.

The device may include a plurality of stencils, wherein each stencil is substantially arcuate shaped. The degree of arc of each of the stencils may be substantially similar and corresponds to the degree of arc of the positioning component. Alternatively, the degree of arc of each successive stencil may be decreased the further each successive stencil is situated from the positioning component. The stencil may include an application surface for receiving a marking medium thereon. In such an instance, the stencil may further include a reservoir fluidly connected to the application surface for storing the marking medium therein.

The positioning component may be an elongated member extending substantially from a middle portion of the template component. The template component may be pivotally attached to the elongated member. Additionally, the device may include means for adjusting the position of the template component along the length of the elongated member.

In another embodiment, a connecting piece may extend from the positioning component and connect the template component thereto. The connecting piece may be a string-like member. In this instance, the positioning component may include a spring-loaded retraction mechanism for receiving the string-like member. The device may include one or more handles attached thereto, such as to the positioning component, the template component, and/or the connecting piece.

Another embodiment of the present invention includes a device for establishing an area of incision on the breast, wherein the device includes (a) a substantially arcuate-shaped member; (b) an elongated member pivotally connected to at one end and extending substantially from a middle portion of the arcuate-shaped member, wherein the device includes means for adjusting the position of the arcuate-shaped member along the length of the elongated member; and, optionally, (c) a positioning component attached to the other end of the elongated member, wherein the positioning component is adapted to be positioned on or adjacent to the NAC of the breast. The positioning component may be substantially circular and sized to substantially matingly receive the nipple of the NAC, or substantially circular and sized to substantially axially align with the nipple of the NAC, or substantially semi-circular and sized to semi-circumferentially abut the periphery of the areola of the NAC.

An exemplary embodiment of a method for establishing an area of incision on a breast includes the steps of: (a) aligning a positioning component on or adjacent to the NAC of the breast; (b) aligning a stencil with a skin line of the breast, wherein the stencil is connected to the positioning component; and (c) forming a curved incision marking or a curved incision on the breast to substantially correspond with the curvature of the skin line of the breast. The method may also include the step of adjusting the distance of the stencil from the positioning component.

Still other desirable features of the invention will become apparent to those of ordinary skill in the art upon reading and understanding the following detailed description, taken with the accompanying drawings, wherein like reference numerals represent like elements throughout.

DESCRIPTION OF THE PREFERRED EMBODIMENTS

The present invention will now be described with reference to the accompanying figures. It is to be understood that the specific devices illustrated in the attached figures and described in the following specification are simply exemplary embodiments of the present invention. Hence, specific dimensions and other physical characteristics related to the embodiments disclosed herein are not to be considered as limiting.

Figure 1:
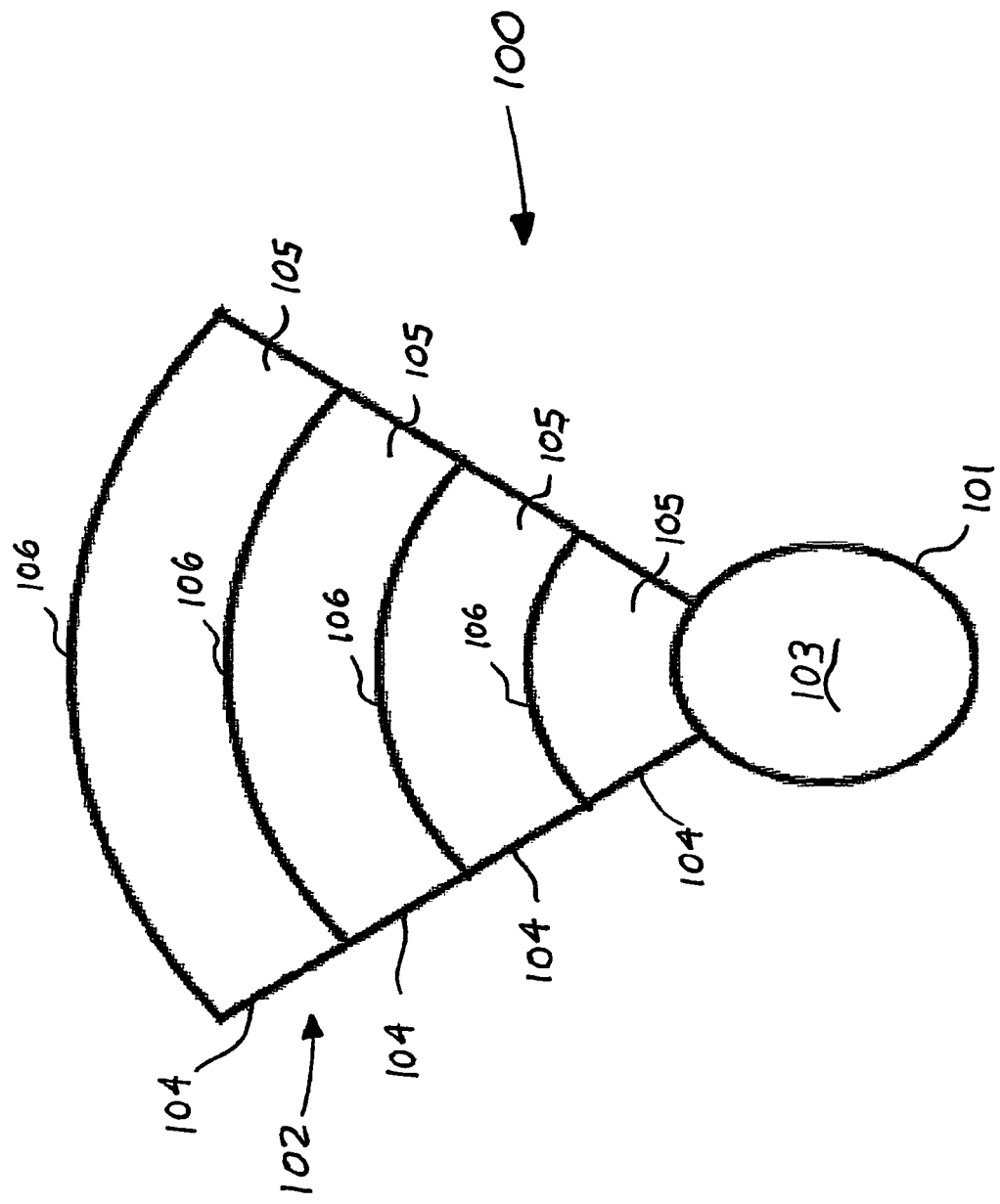
FIG. 1 is a front plan view of a first embodiment breast incision optimizing device in accordance with the present invention.
Figure 5:
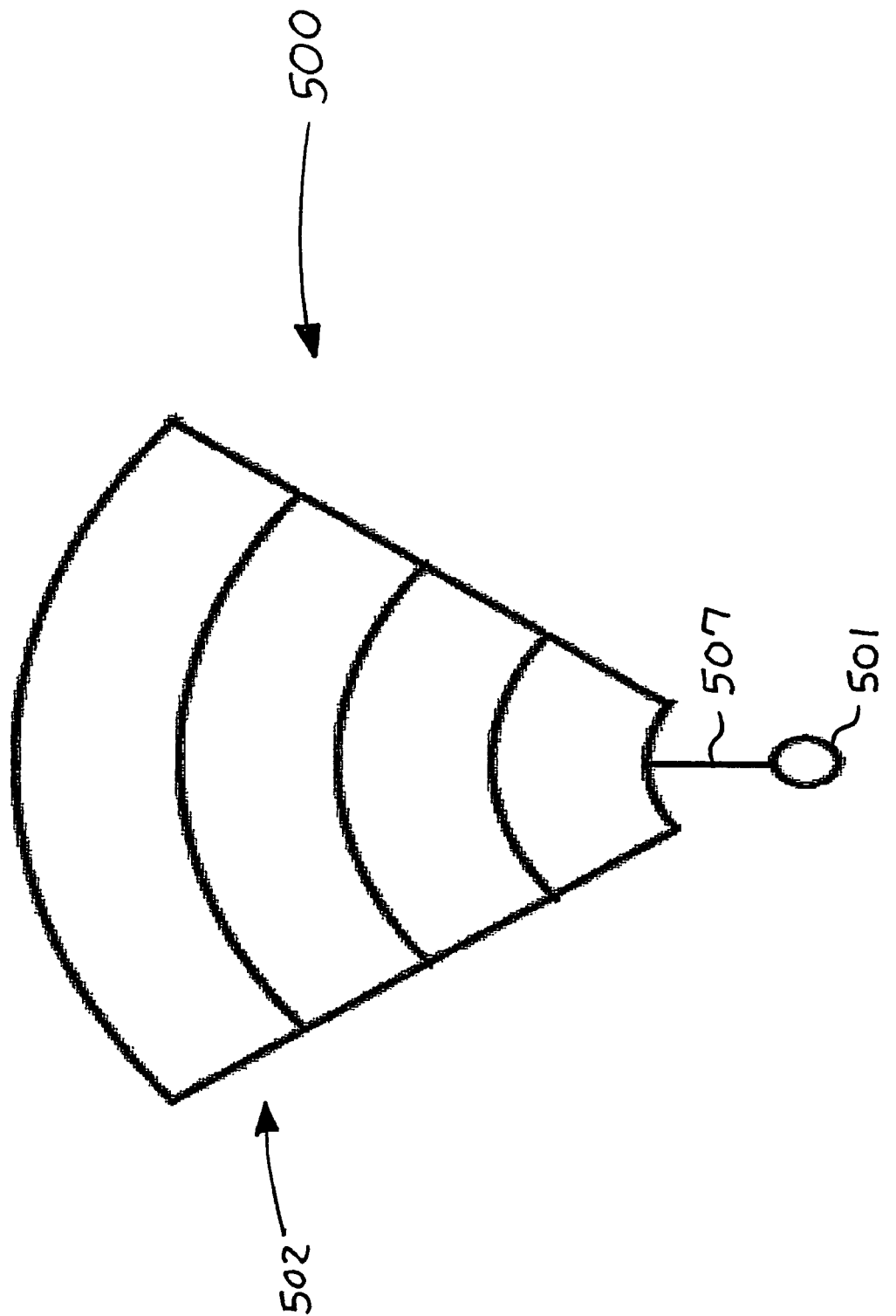
FIG. 5 is a front plan view of a fifth embodiment breast incision optimizing device in accordance with the present invention.

FIG. 1 depicts a breast incision optimizing device 100 designed to function as a guide for making incisions on a breast using the nipple areola complex (NAC) thereof as a reference point. In general, the device 100 includes a positioning component 101 and a template component 102. With respect to FIG. 1, the positioning component 101 is substantially circular defining an open area 103 therein through which the nipple and areola are visible. The positioning component 101 is adapted to orient the device 100 on the breast with respect to the NAC. Accordingly, the positioning component 101 will be aligned with the NAC such that the NAC may be visualized through the open area 103 of the positioning component 101. It is to be understood that the size of the positioning component 101 may vary. For example, the positioning component 101 may be sized to encompass only the nipple, as shown in FIG. 5. Alternatively, an intermediately sized positioning component 101 may be sized to only encompass a portion of the areola. In any case, the correct alignment of the positioning component 101 with respect to the NAC allows the device 100 to be rotated around an axis of the NAC (e.g., nipple).

The template component 102 is defined as a series of substantially curvilinear or arcuate stencils 104 through which breast tissue is visible. In the desirable embodiment, the template component 102 includes four integral stencils 104, each defining an open area 105. Each stencil 104 includes an arc portion 106 to allow a marking instrument, such as an ink marker, to trace along the arc 106. Therefore, the stencils 104 should be sufficiently smooth and rigid to allow the ink marker to travel in a continuous and evenly curved manner along either an inner or outer edge of the arc portion 106. Desirably, the arc portions 106 are connected at the ends thereof to radial supports or other structures extending from the positioning component 101 or an adjacent stencil. Thus, the construction of the stencils 104 may be viewed as a combination of the radial supports with the arc portions 106. It is to be understood that the number of stencils 104, the length or width of each stencil 104, and the degree of each arc portion 106 may vary. As shown in FIG. 1, the overall distance of the template component 102 with respect to the positioning component 101 is fixed. The device 100 may be constructed of plastic, metal, a combination thereof, or any other suitable material.

Several embodiments utilizing various templates and the positioning components are described herein. It is to be understood that the components, features, and characteristics of any one of these embodiments may be interchangeable, thereby resulting in additional breast incision optimizing devices not specifically discussed herein.

Figure 2:
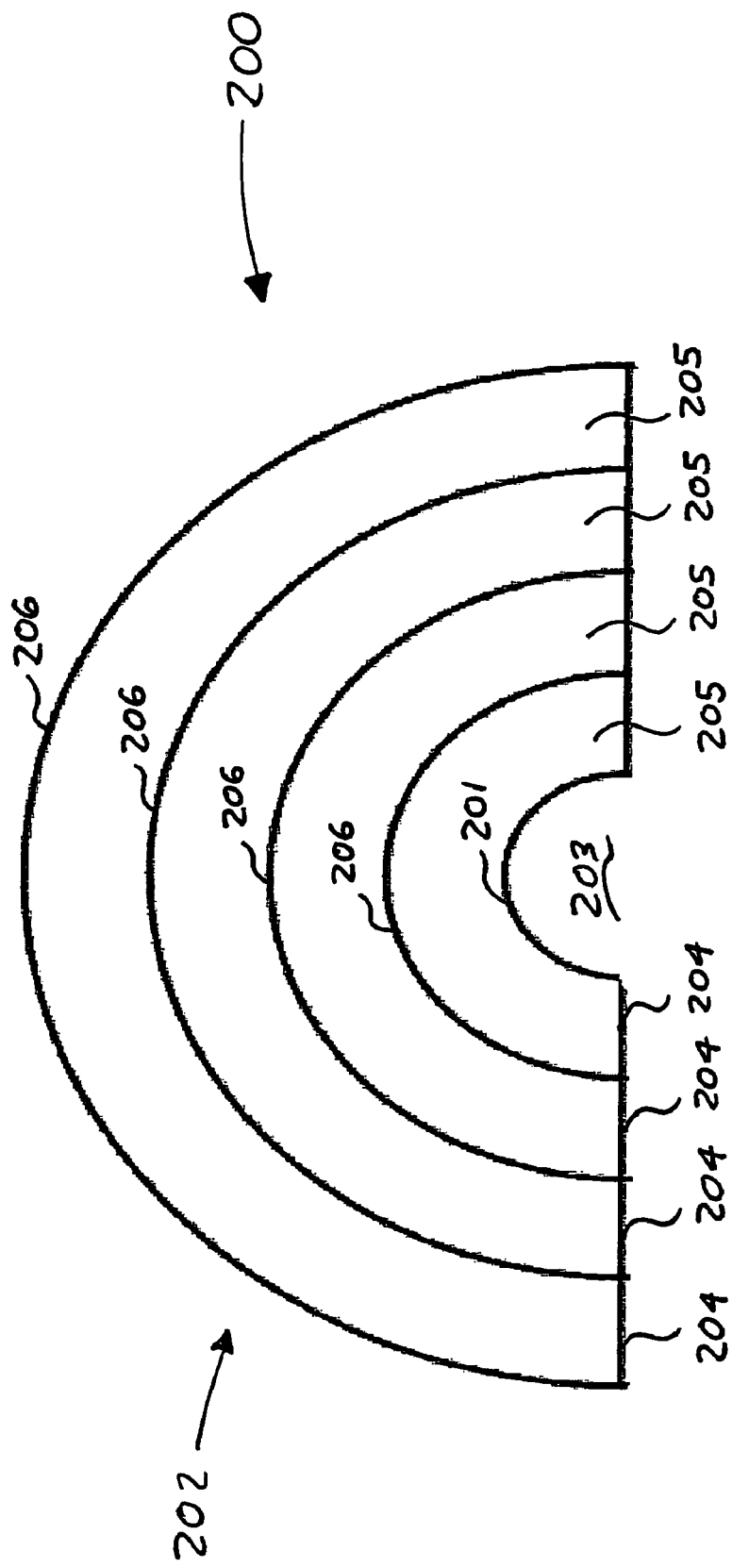
FIG. 2 is a front plan view of a second embodiment breast incision optimizing device in accordance with the present invention.
Figure 3:
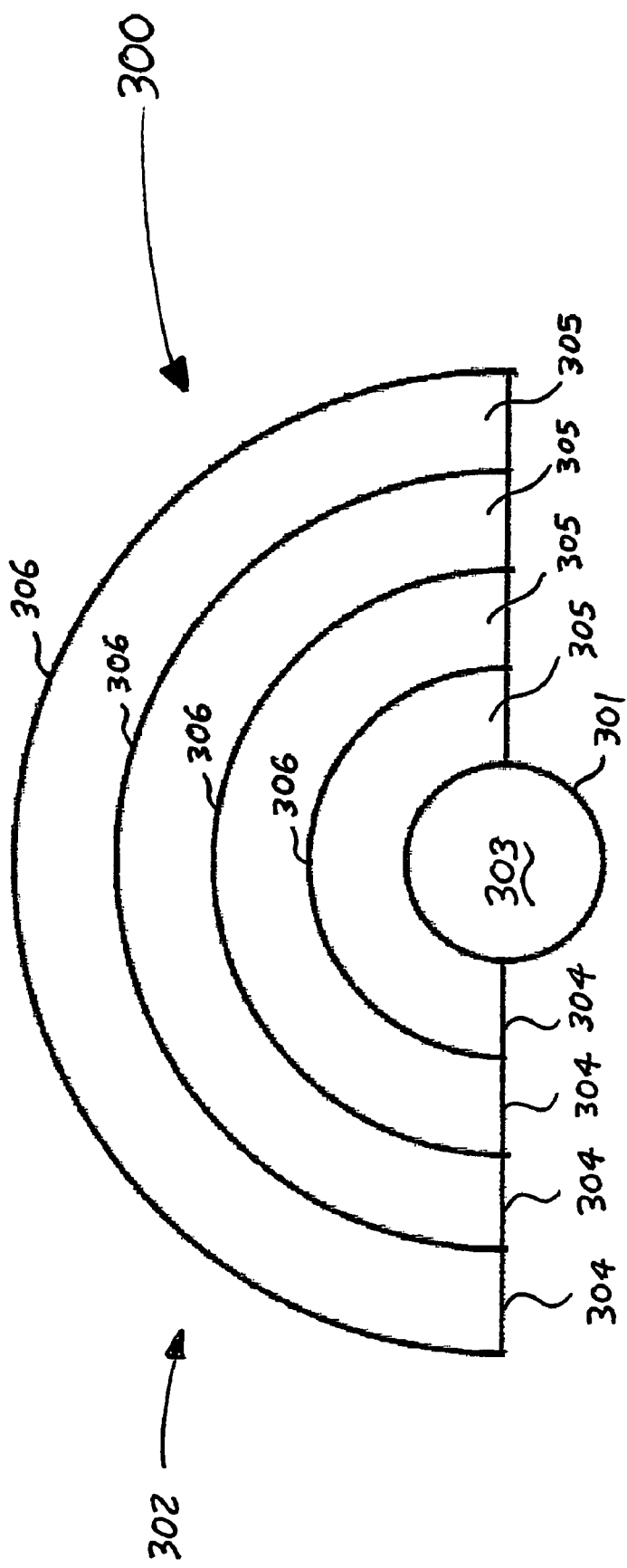
FIG. 3 is a front plan view of a third embodiment breast incision optimizing device in accordance with the present invention.

FIGS. 2 and 3 depict second and third embodiment breast incision optimizing devices 200, 300, respectively. The devices 200, 300 include substantially semi-circular template components 202, 302, respectively. However, the device 200 includes a substantially semi-circular positioning component 201, whereas the device 300 includes a substantially circular positioning component 301. Similar to the device 100, devices 200, 300 include respective open areas 203, 303. The open areas 203, 303 are sized to align with a portion, either partially or completely, of the NAC. For example, the open area 203 may be centered on the areola or nipple, whereas, the open area 303 may be aligned with a circumferential edge of the areola or nipple. The devices 200, 300, also include corresponding characteristics depicted in the device 100 of FIG. 1. For example, the devices 200, 300 include respective stencils 204, 304 with open areas 205, 305 and arc portions 206, 306. Similarly, the devices 206, 306 may be used to visualize the breast through the open areas 203, 303, whereby the stencils 204, 304 may be used to draw lines on the breast that will be used as guides for making incisions thereafter.

Figure 4:
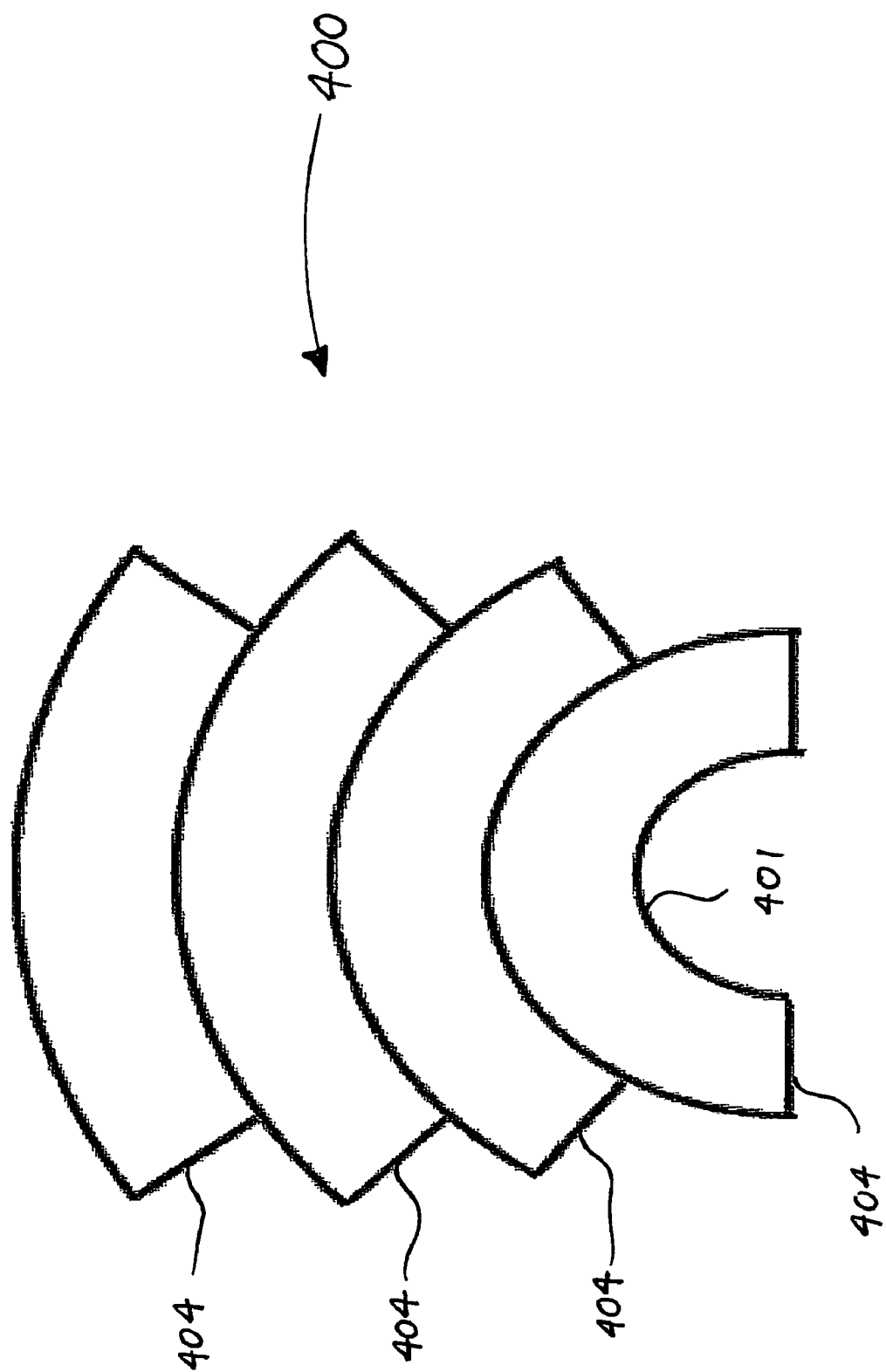
FIG. 4 is a front plan view of a fourth embodiment breast incision optimizing device in accordance with the present invention.

FIG. 4 depicts a fourth embodiment breast incision optimizing device 400. The template component 402 includes stencils 404 that are substantially similarly sized and shaped with respect to each other. This is contrary to the stencils 104, 204, 304 depicted in the devices 100, 200, 300, respectively. It is to be understood that the positioning component 401 may be semi-circular, as shown, or may be completely circular. This is in an instance in which features of other embodiment breast incision optimizing devices may be incorporated or interchanged with each other.

FIG. 5 depicts a fifth embodiment breast incision optimizing device 500. The device 500 includes a template component 502 similar to the template component 102 of FIG. 1. However, the positioning component 501 is sized to be aligned with the nipple. The device 500 includes a connecting piece 507 for securing the template component 502 to the positioning component 501.

Figure 6:
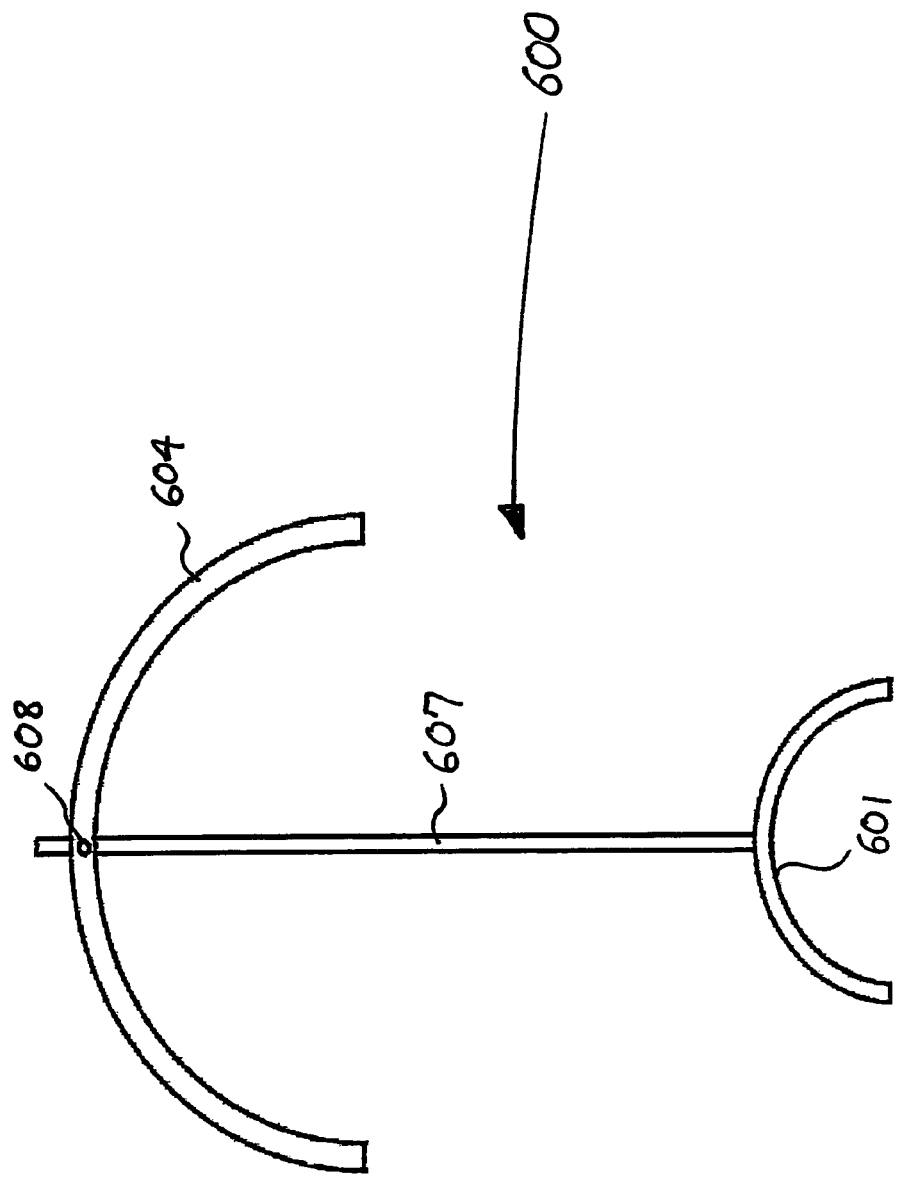
FIG. 6 is a front plan view of a sixth embodiment breast incision optimizing device in accordance with the present invention.
Figure 12:
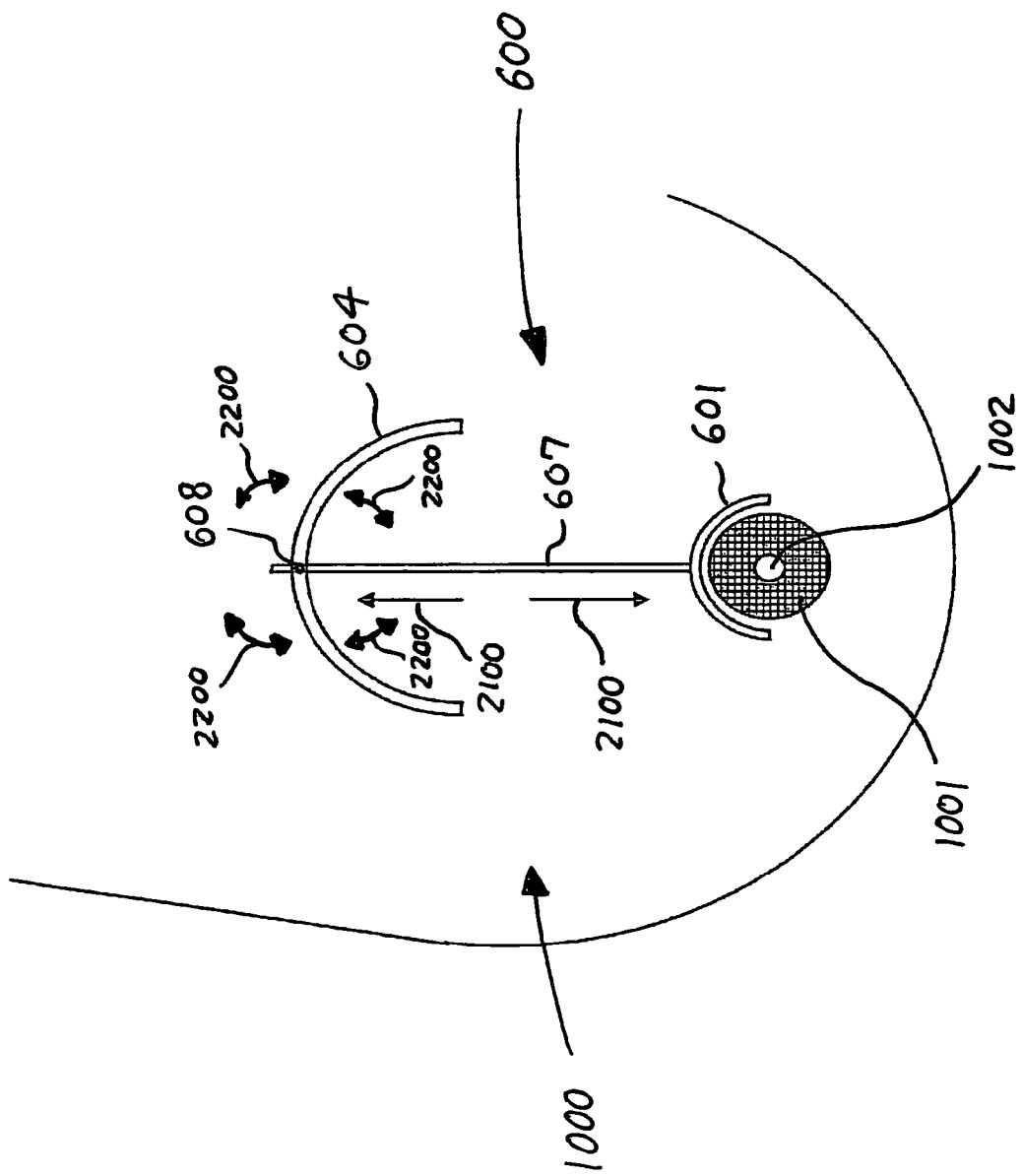
FIG. 12 is a front plan view of the sixth embodiment breast incision optimizing device positioned on the breast.
Figure 13:
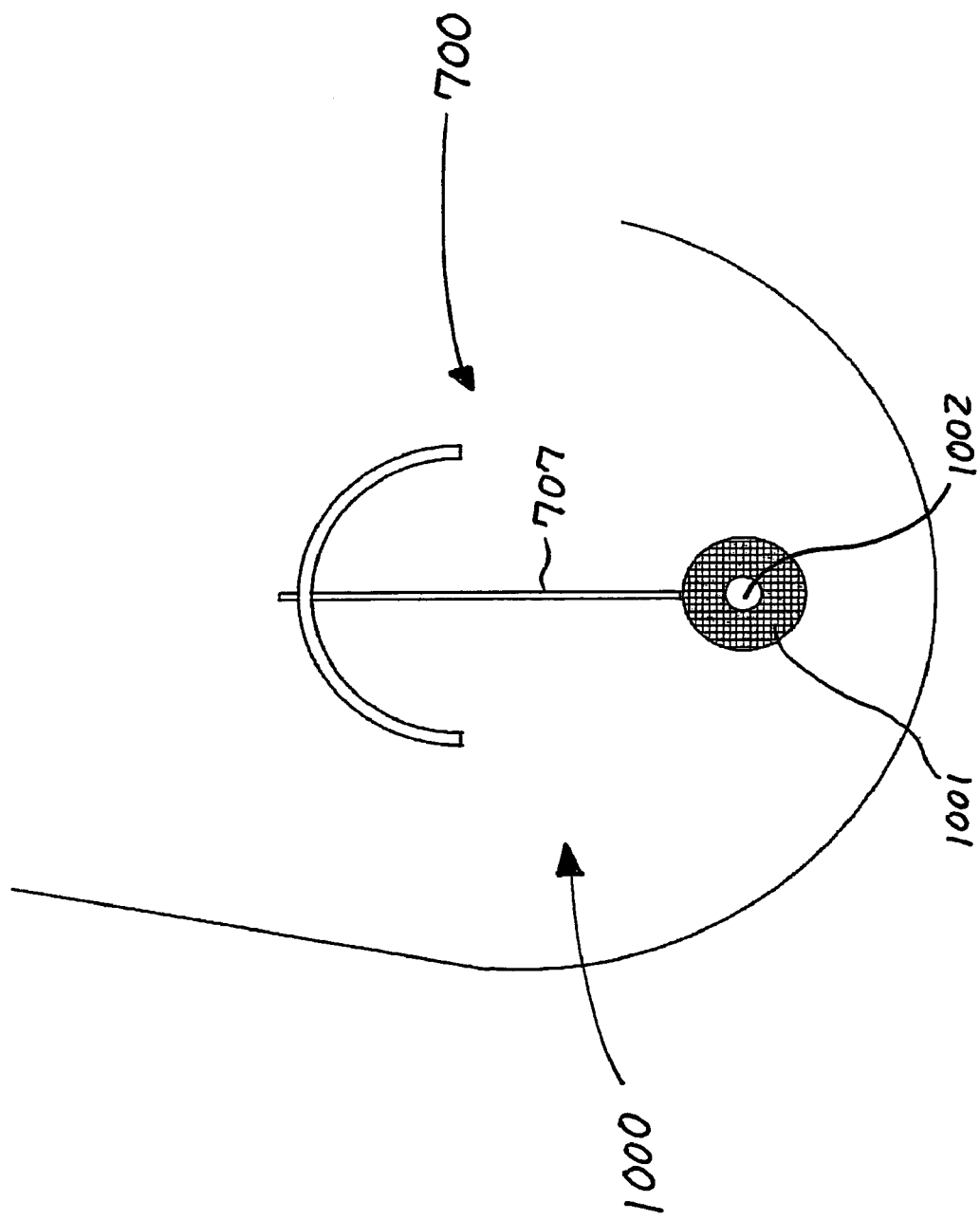
FIG. 13 is a front plan view of the seventh embodiment breast incision optimizing device positioned on the breast.

FIG. 6 depicts a sixth embodiment breast incision optimizing device 600. The device 600 includes a single stencil 604 movably secured to a connecting piece 607 extending from a positioning component 601. Desirably, the connecting piece 607 is secured at a midpoint of the stencil 604 or substantially near a middle portion thereof. A securing mechanism, such as a threadable knob 608, may be used to secure the stencil 604 along various positions along the connecting piece 607. This allows the single stencil 604 to provide the function offered by a multiple stencil arrangement, such as is shown in FIG. 1. The stencil 604 may include a sleeve (not shown) through which the connecting piece 607 is inserted. Alternatively, the connecting piece 607 may include a plurality of holes into which the threadable knob 608 may secured. It is to be understood that any suitable securing mechanism having linear movement capabilities may be utilized as would be known to those having ordinary skill in the art. As shown in FIG. 12, the stencil 604 may also be adapted to pivotally rotate around its axis of fixation (e.g., threadable knob) to provide additional positions conducive to optimizing an incision on the breast. It is to be understood that the stencil 604 may be removable and may be exchanged for other stencils of various lengths and/or degrees of arc. As in the previous embodiments, the positioning component 601 may be of various sizes to accommodate various areas of the NAC and may be of various shapes, including semi-circular and circular.

Figure 7:
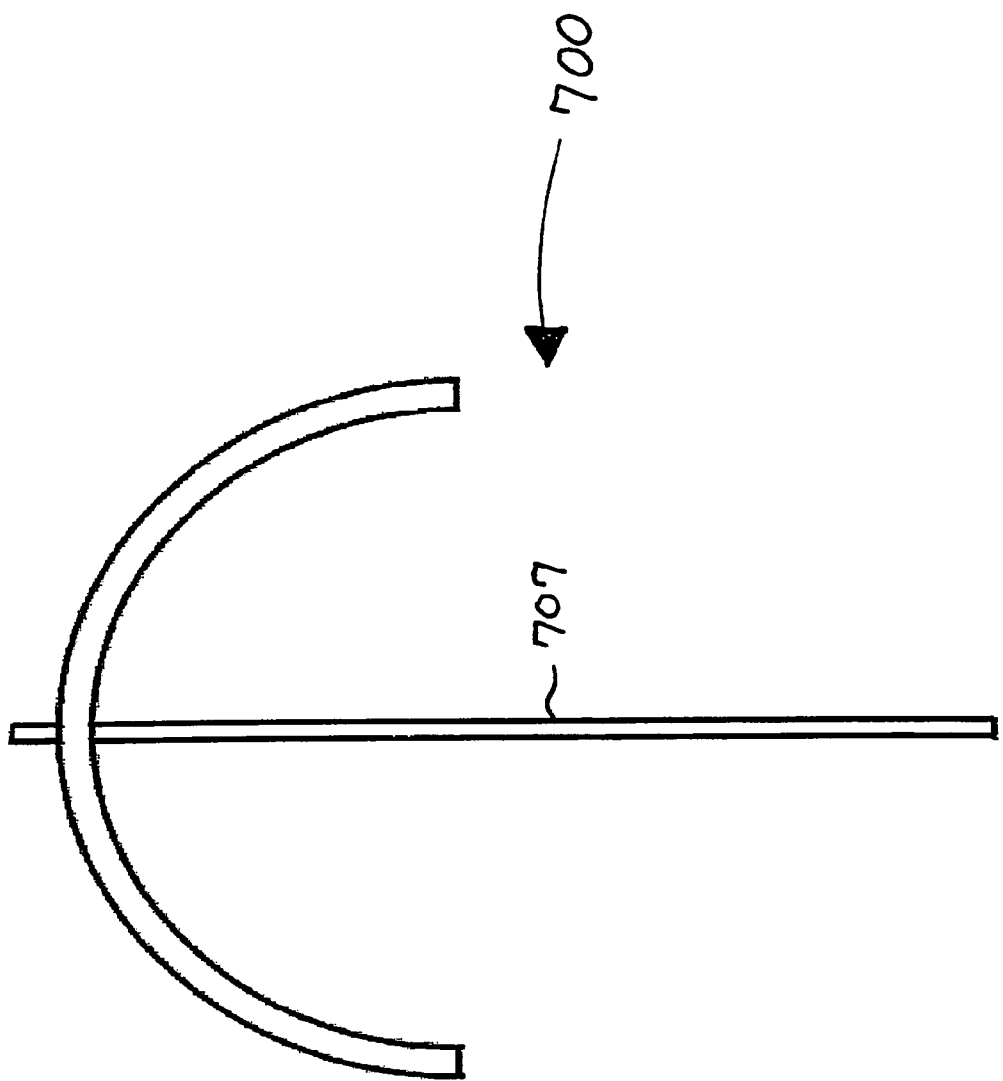
FIG. 7 is a front plan view of a seventh embodiment breast incision optimizing device in accordance with the present invention.

FIG. 7 depicts a sixth embodiment breast incision optimizing device 700. The device 700 is similar to the device 600 except for the lack of a positioning component attached to a connecting piece 707. Accordingly, the unattached end of the connecting piece 707 is placed perpendicular to the NAC, or alternatively, the unattached end may be aligned with the center of the nipple.

Figure 8:
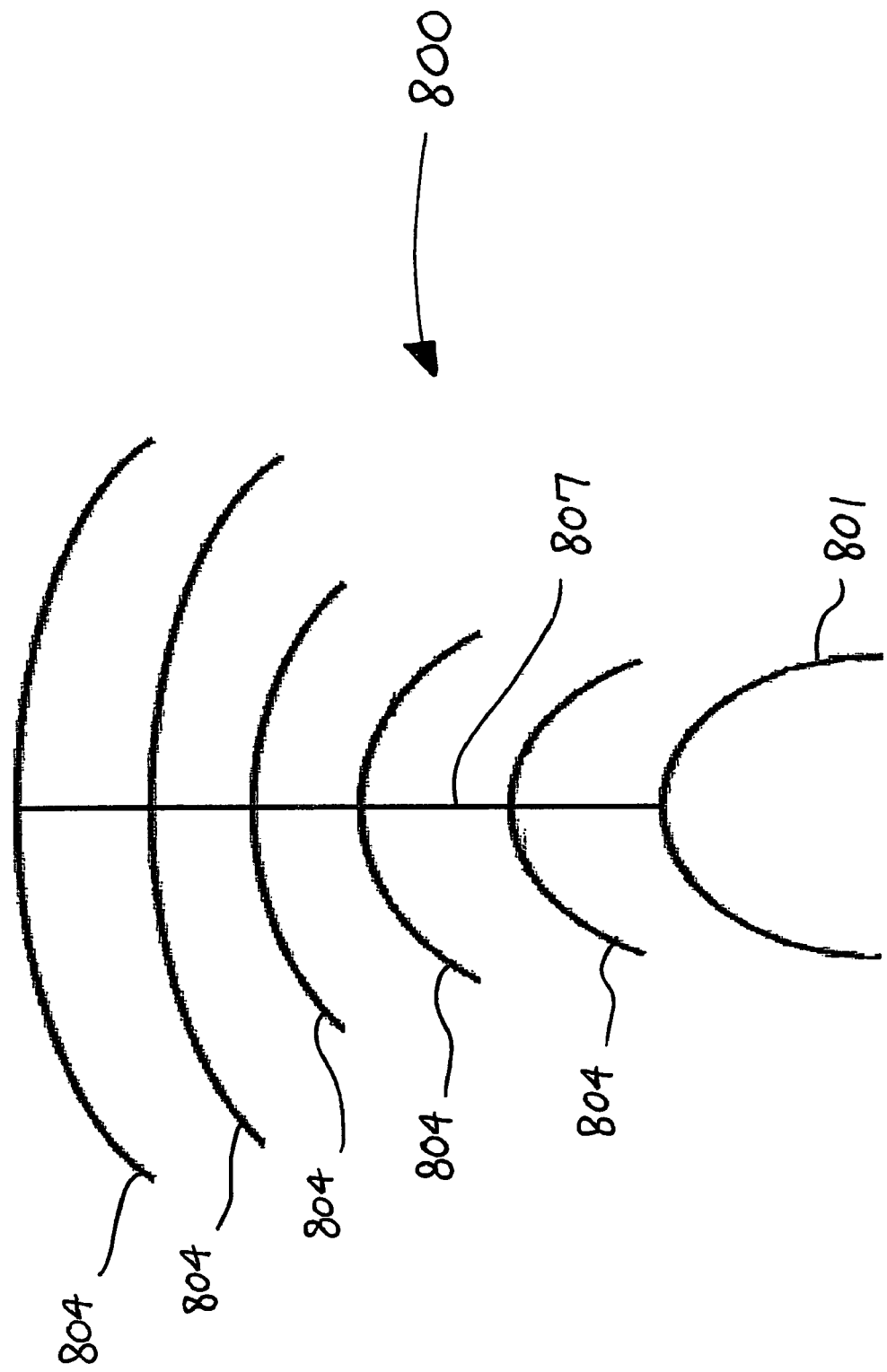
FIG. 8 is a front plan view of an eighth embodiment breast incision optimizing device in accordance with the present invention.
Figure 9:
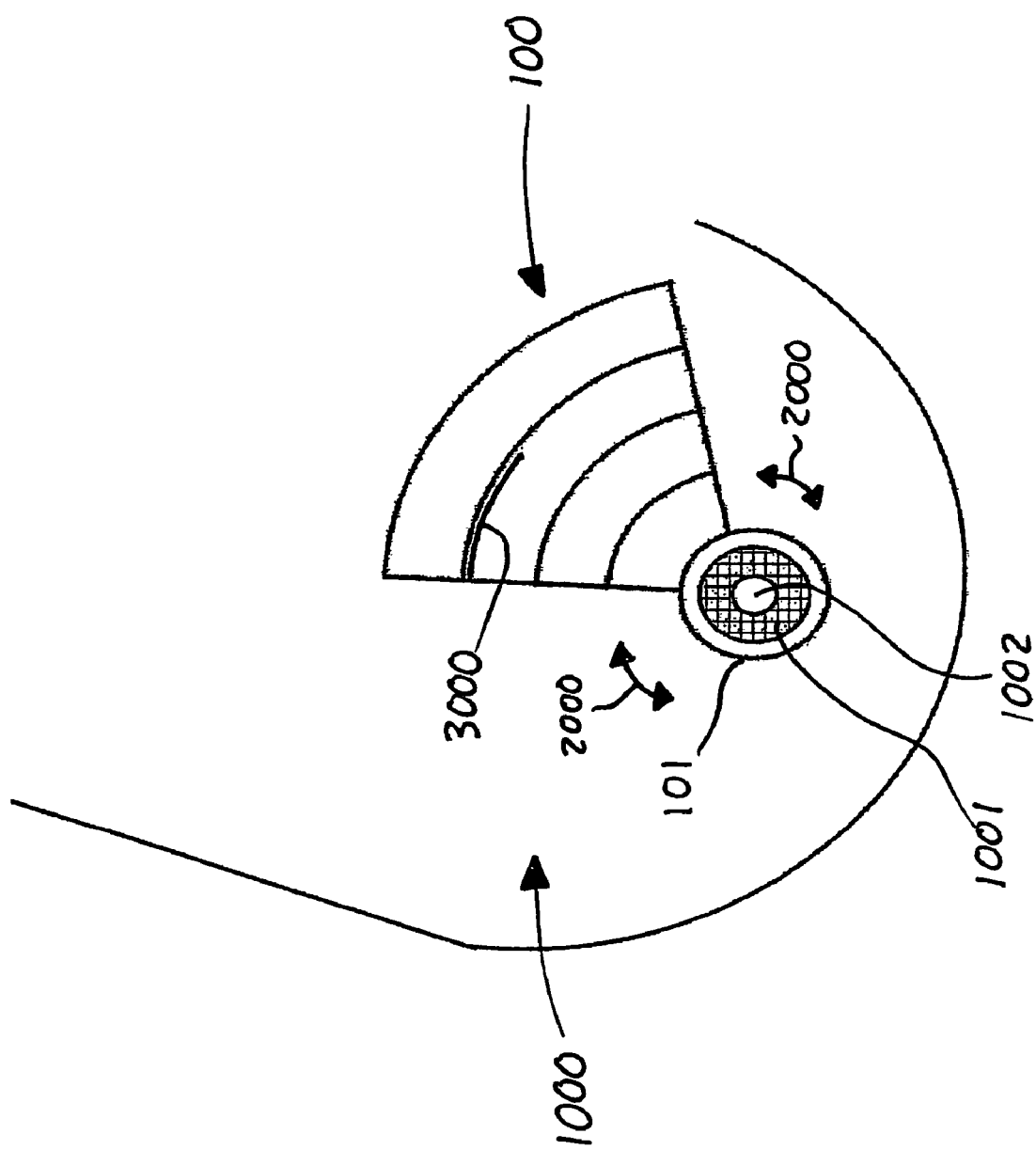
FIG. 9 is a front plan view of the first embodiment breast incision optimizing device positioned on the breast.
Figure 10:
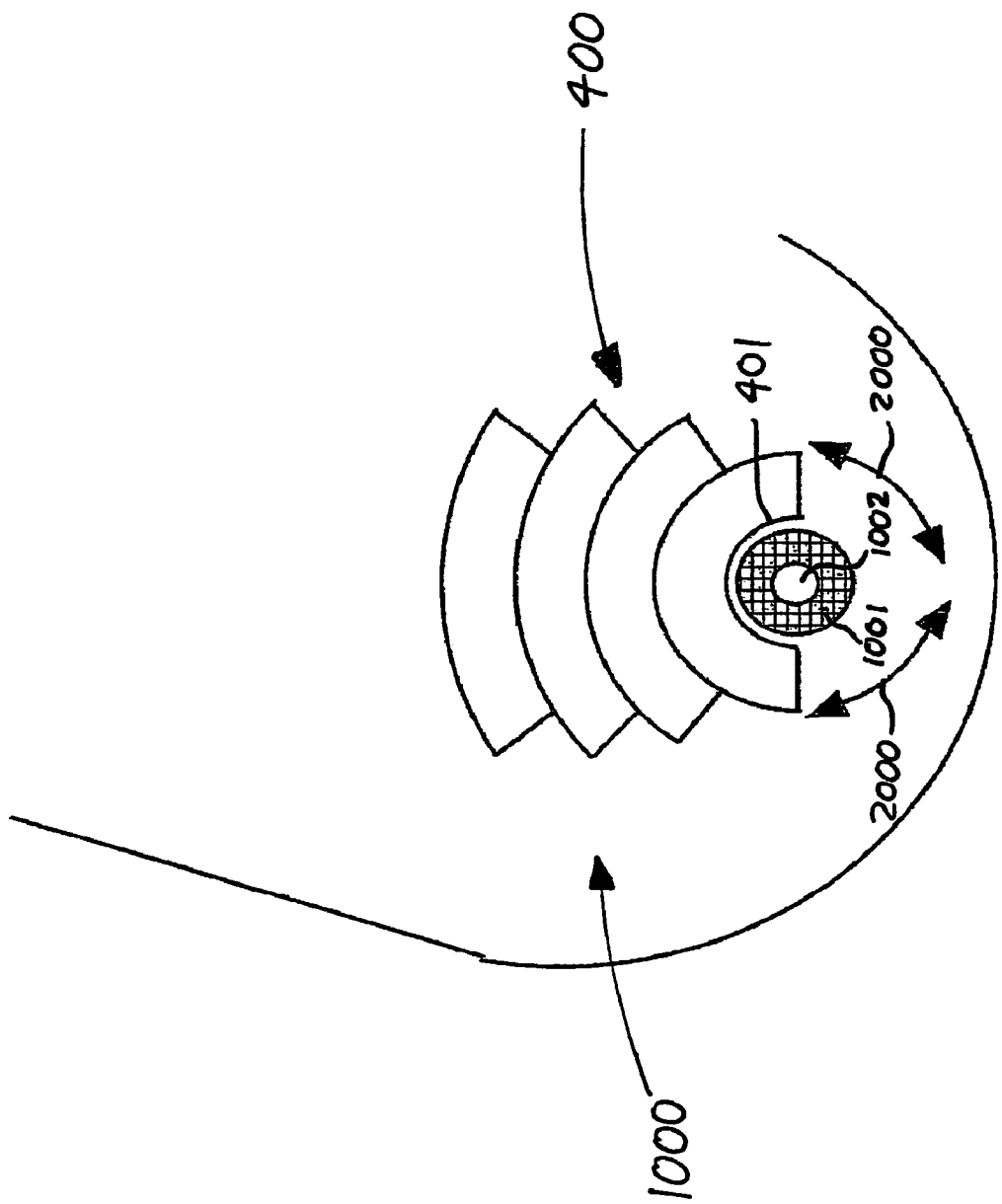
FIG. 10 is a front plan view of the fourth embodiment breast incision optimizing device positioned on the breast.
Figure 11:
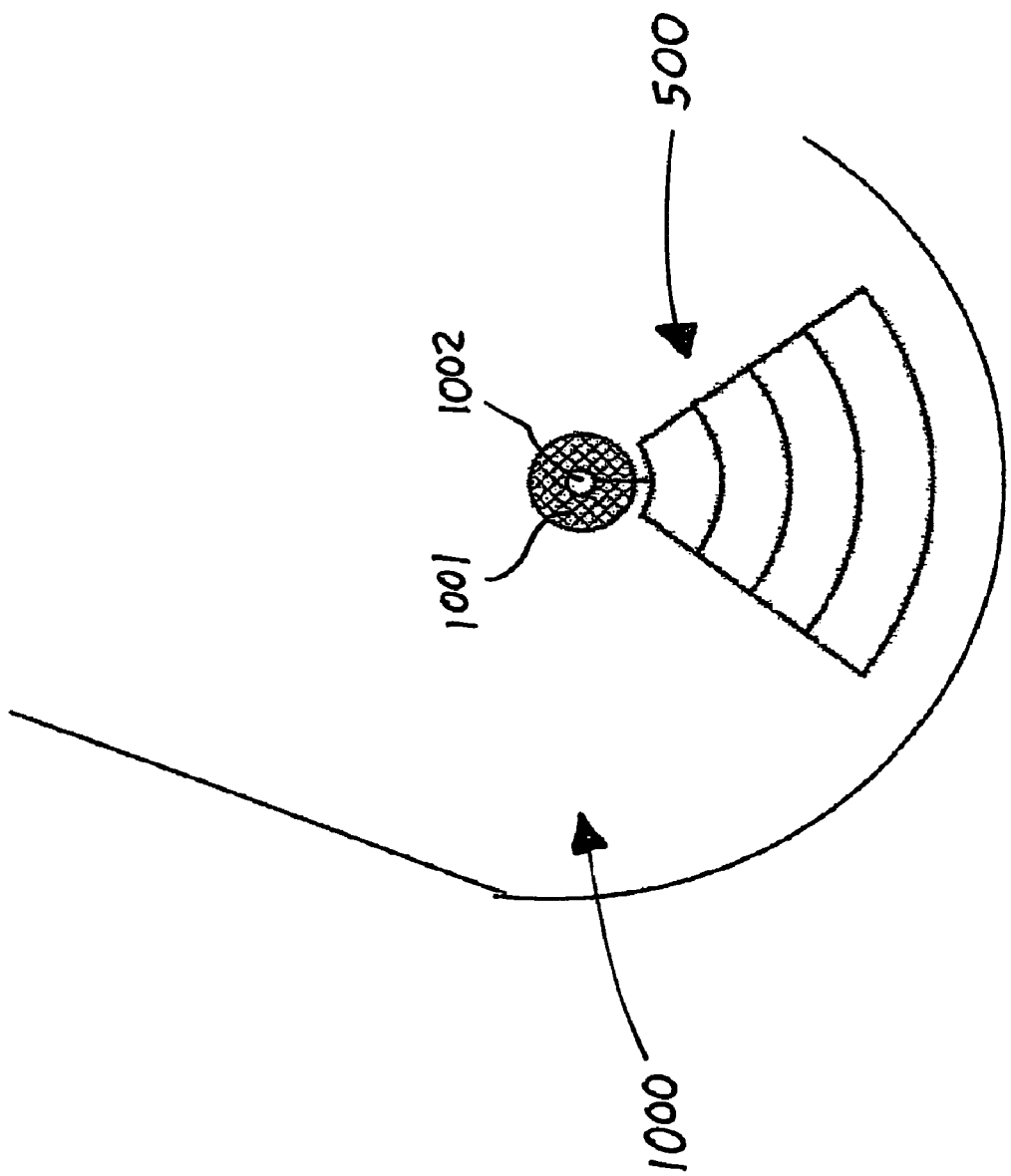
FIG. 11 is a front plan view of the fifth embodiment breast incision optimizing device positioned on the breast.

FIG. 8 depicts an eighth embodiment breast incision optimizing device 800. The device 800 includes a plurality of stencils 804 positioned on a connecting piece 807. As shown, the stencils 804 are of varying length and degree of arc. Desirably, the stencils 804 decrease in degree of arc and increase in length as they are situated further away from the positioning component 801.

In general usage, the device 100 allows an individual, such as a surgeon, to either trace a line or directly make a line on the breast which thereafter may be used to make an optimal incision thereon. An optimal incision may be regarded as an incision that follows the skin lines of the breast, thereby minimizing the appearance of scarring. FIGS. 9, 10, 11, 12, and 13 depict the first, fourth, fifth, sixth, and seventh embodiment breast incision optimizing devices, respectively, positioned on a breast 1000 having a NAC including an areola 1001 and a nipple 1002. With respect to FIG. 9, the device 100 is positioned on the breast 1000 using the areola 1001 as the reference point. Specifically, the positioning component 101 is positioned to circumferentially encompass the areola 1001. The device 100 may be rotated in the directions of the arrows 2000 to allow any tissue portion of the breast to be marked. An incision or mark 3000 may be made by guiding the scalpel or ink marker, respectively, along the arc portion 106 of one of the stencils 104. Similarly, in FIG. 10, the positioning component 401 of the device 400 is positioned to semi-circumferentially abut the periphery of the areola 1001. With respect to FIG. 11, the device 500 is positioned on the breast 1000 using the nipple 1002 as the reference point. With respect to FIG. 12, the positioning component 601 of the device 600 is positioned to semi-circumferentially abut the periphery of the areola 1001. The threadable knob 608 may be loosened and then, as indicated by the arrows 2100, the stencil 604 may be moved along the length of the connecting piece 607. Thereafter, the threadable knob 600 may be tightened to secure the stencil 604 in a new position with respect to the connecting piece 607. Arrows 2200 indicate the rotational movement of the stencil 604 around its fixed axis. It is to be understood that other rotational mechanisms may be implemented with any of the embodiments discussed herein. With respect to FIG. 13, the connecting piece 707 of the device 700 is positioned adjacent to the areola 1001, as shown, or alternatively adjacent to the nipple 1002.

Figure 14:
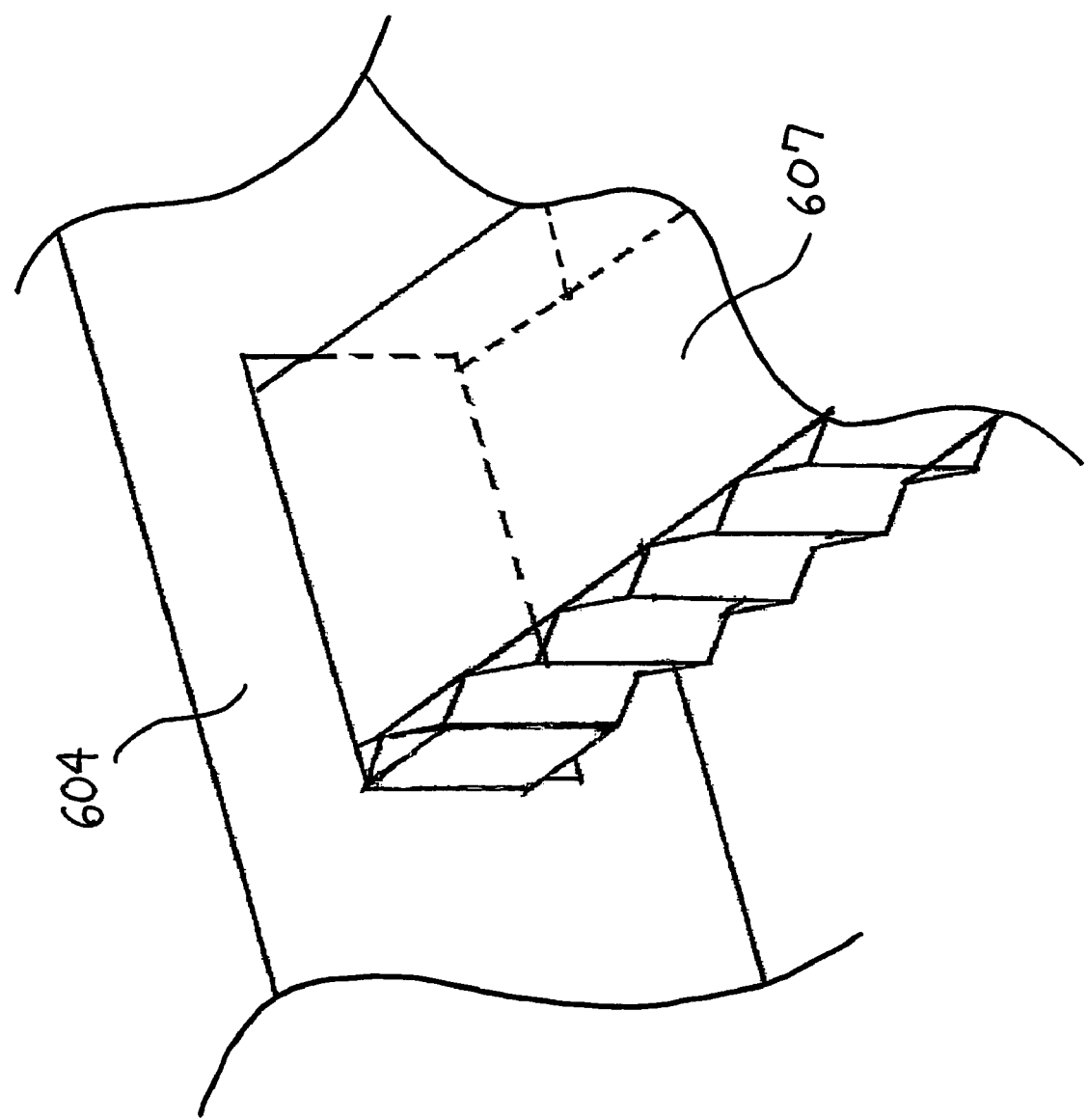
FIG. 14 is a partial exploded view of an adjustable length interface for use with the present invention.

FIG. 14 depicts an adjustable length interface for use with any suitable embodiment of the present invention, such as the devices 600, 700. Instead of utilizing a threadable knob 608, the device 600 may include an interlocking pressure deformable configuration. For example, the stencil 604 and the connecting piece 607 may include a correspondingly mateable "peak and valley" arrangement. Both the stencil 604 and the connecting piece 607 may be constructed of resilient plastic that allows the respective "peaks and valleys" to engage and disengage each other as the stencil 604 is moved along the length of the connecting piece 607. Desirably, the adjustable length interface allows the template component 602 to be readily movable via minimal exertion of force, yet maintain a sufficient degree of non-movement of the template component 602 when a marking is made therewith. Based upon the description of the aforementioned securing mechanisms, it is to be understood that various other adjustable length interfaces with respect to the stencil position may be implemented, as would be known to those having ordinary skill in the art.

Figure 15:
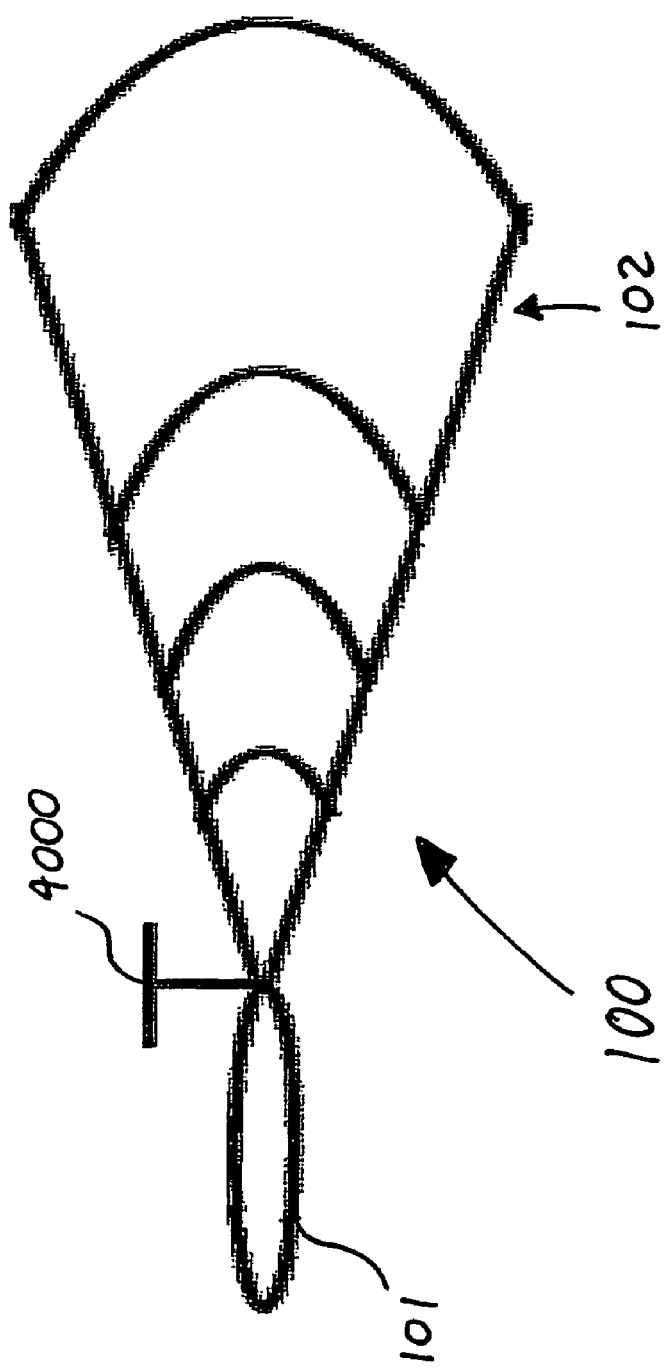
FIG. 15 is a front plan view of the first embodiment breast incision optimizing device having a handle.
Figure 16:
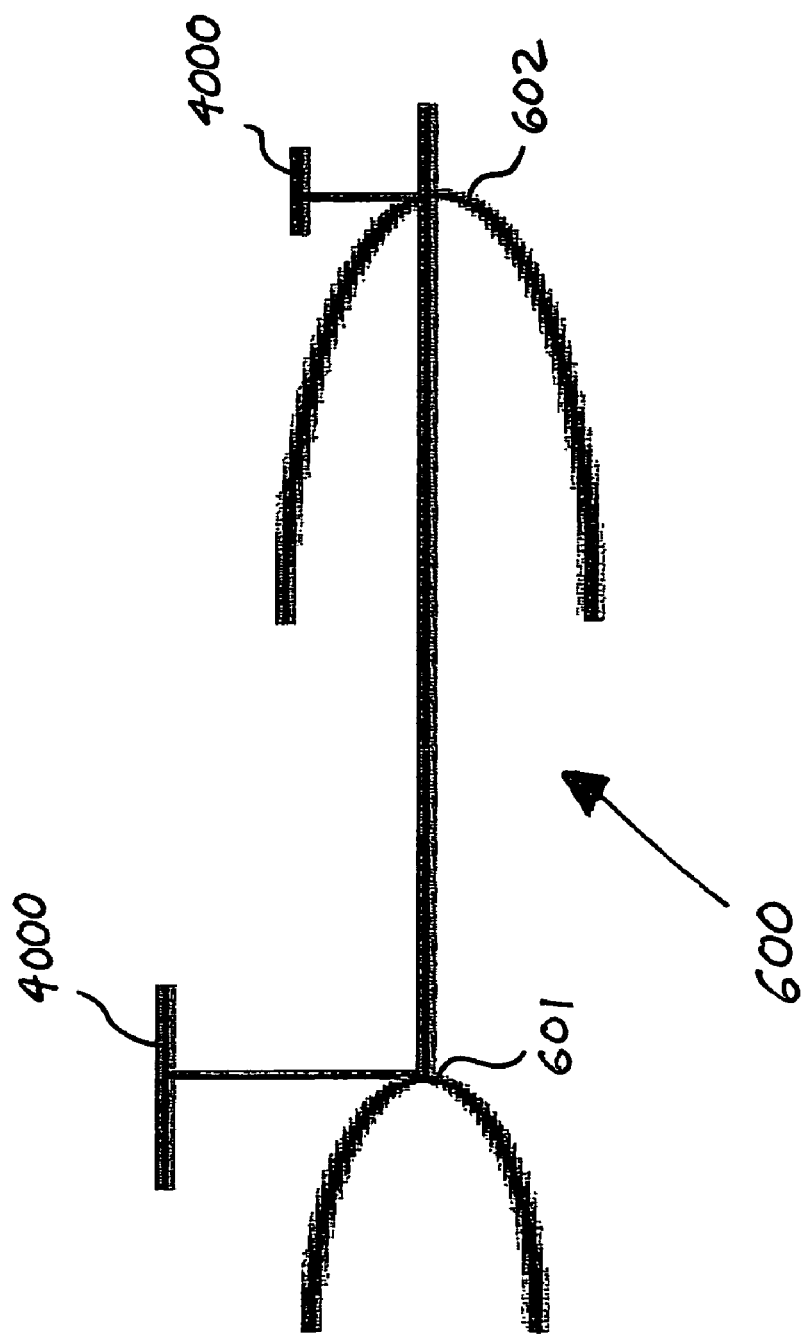
FIG. 16 is a front plan view of the sixth embodiment breast incision optimizing device having handles.

FIGS. 15 and 16 depict the incorporation of handles 4000 in the devices 100, 600. The handles 4000 may be situated on the respective positioning components 101, 601 and/or on the template component 602. In any case, it is to be understood that the shape, dimension, and location of the handles 4000 may vary based upon the embodiment and application thereof. The handles 4000 allow for stabilization of the device on the breast 1000 during use and/or facilitate the rotation of the devices 100, 600 around the NAC. In an alternative embodiment, an adhesive may be used along the underside of any suitable portion of the device to temporarily affix the device to the breast 1000 while the necessary marking is made.

Figure 17:
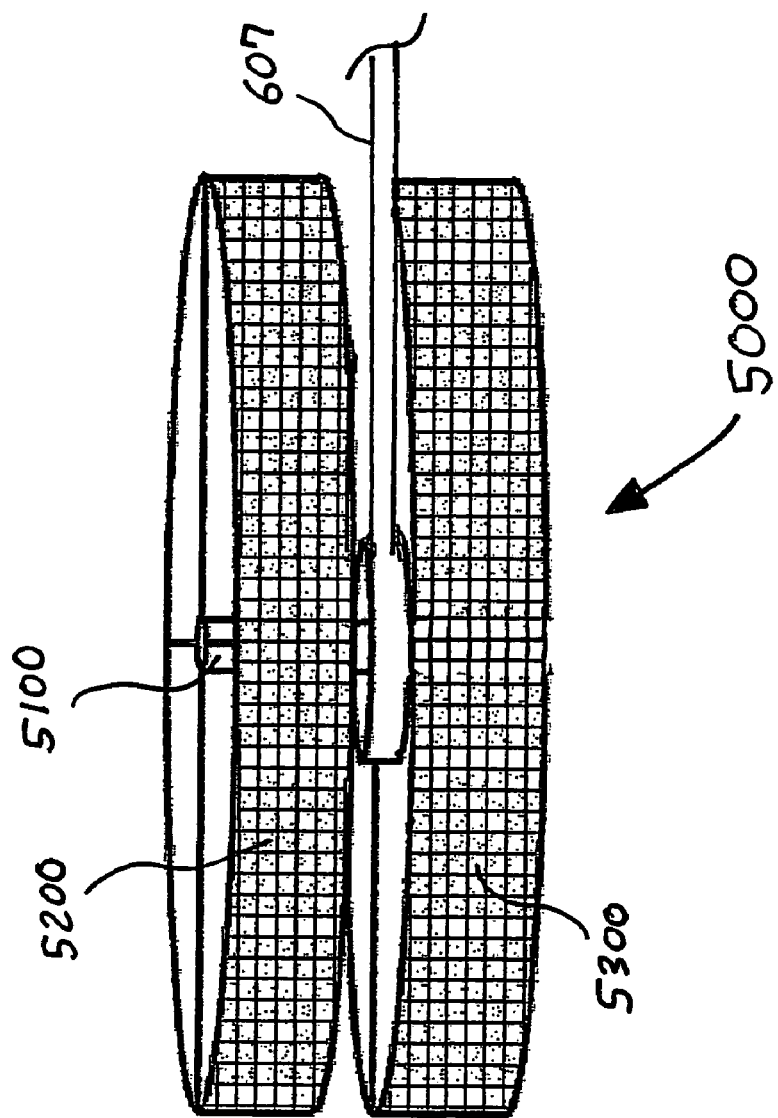
FIG. 17 is a side plan view of a rotatable piece for use with a positioning component of any suitable aforementioned breast incision optimizing device.

FIG. 17 depicts an alternative embodiment positioning component 5000 having a shaft 5100 connected between a first and optionally second member 5200, 5300. A new or existing connecting piece, such as the connecting piece 607, is rotatably secured to the shaft 5100. The connecting piece 607 may rotate around the shaft within the space defined between the first and second members 5200, 5300. The first and second members 5200, 5300 are sized to be aligned with the NAC or a portion thereof. During use of the alternative embodiment positioning component 5000, the first and second members 5200, 5300 remain stationary with respect to the NAC, whereas the connecting piece 607 may move in a circumferential manner around the breast 1000.

Figures 18A, 18B:
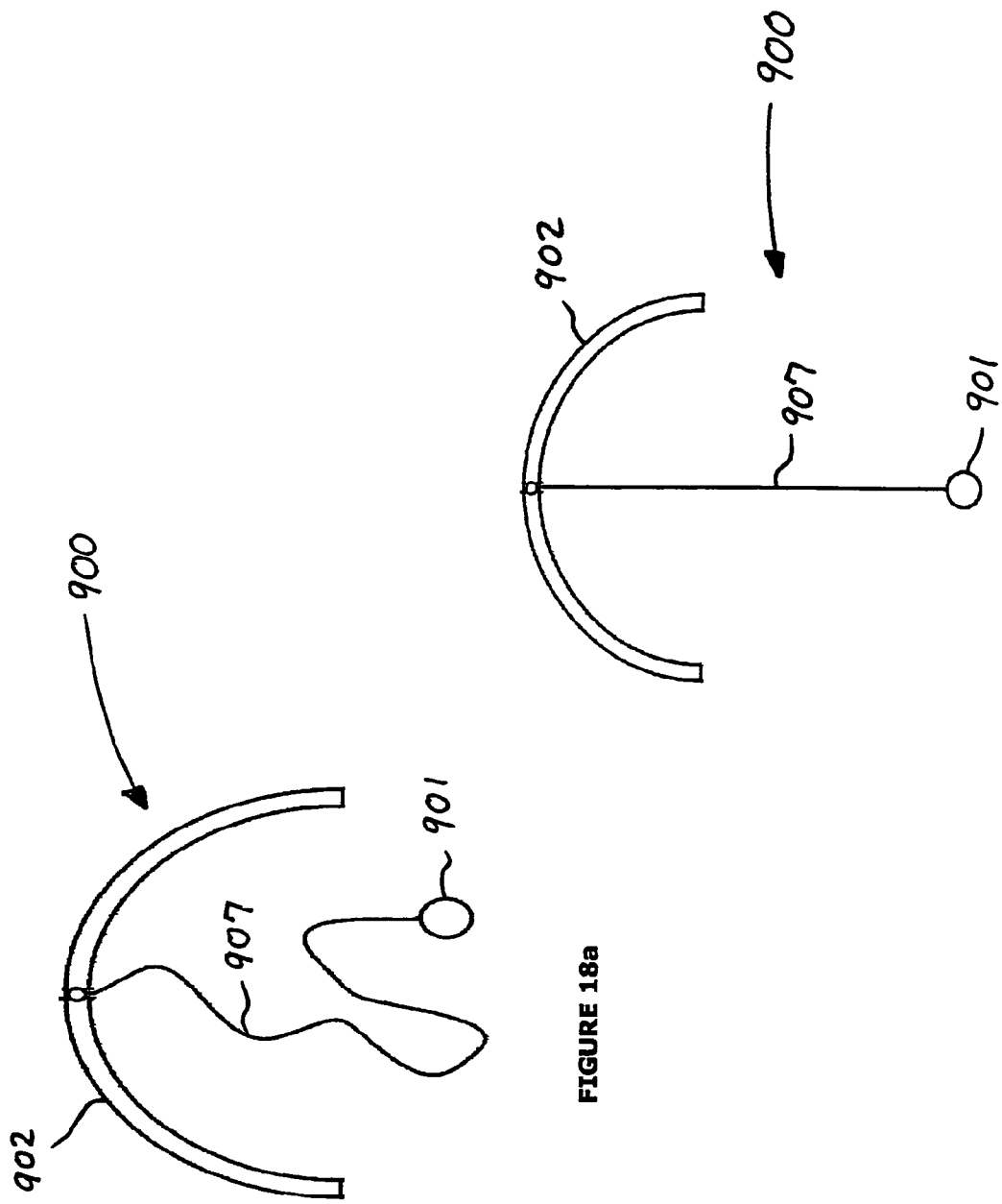
FIG. 18a is a front plan view of a ninth embodiment breast incision optimizing device in an untaut state in accordance with the present invention.
FIG. 18b is a front plan view of the ninth embodiment breast incision optimizing device in a taut state in accordance with the present invention.

FIGS. 18a and 18b depict a ninth embodiment breast incision optimizing device 900. The device 900 includes a connecting piece 907 embodied as a wire or string-like (e.g., non-rigid) member. The connecting piece 907 is connected to a template component 902 and a positioning component 901 at its respective ends. In the device 900, the template component 902 embodies the stencil. The positioning component 901 may include a spring-loaded retraction mechanism (not shown) for automatically spooling or reeling in the connecting piece 907 to be stored within the positioning component 901 when the device 900 is not in use. As with the previously-discussed positioning components, the positioning component 901 is adapted to be aligned with the NAC or a portion thereof. The connecting piece 907 may be pulled from within the positioning component 901 when the device 900 is to be used. Specifically, the connecting piece 907 may be pulled taut at various lengths thereof to facilitate marking of the breast 100 via the connected template component 902 or stencil.

Figure 19:
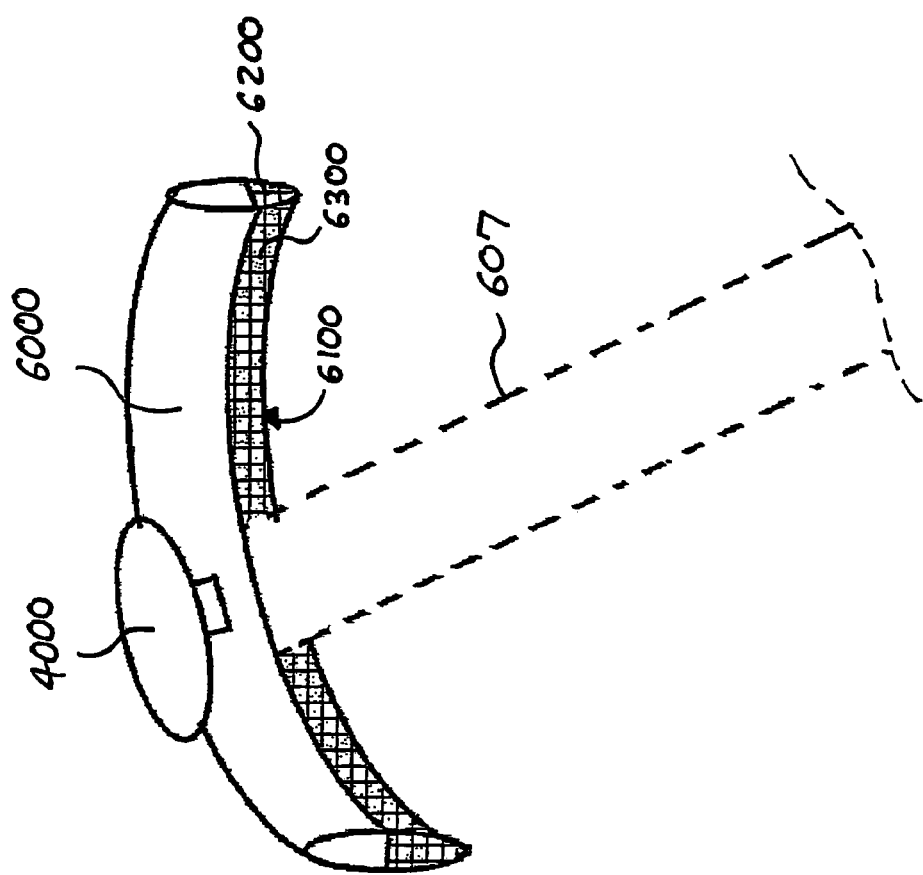
FIG. 19 is a perspective view of an ink-transferring component for use independently of or in connection with a positioning component of any suitable aforementioned breast incision optimizing device.

FIG. 19 depicts an alternative embodiment stencil 6000 for use with any suitable aforementioned device, such as the devices 100, 600. In general, the stencil 6000 functions to transfer ink and, thereby, directly mark the desired line on the breast 1000. This is in contrast to the aforementioned stencils in which such stencils only act as a guide for a separate marking device. Specifically, in a desirable embodiment, the stencil 6000 includes an application surface 6100 fluidly connected to a reservoir 6200 having ink 6300 or any other suitable marking medium contained therein. An exemplary embodiment of the application surface 6100 may be the felt material used in connection with the tips of marking pens. In an alternative embodiment, the stencil 6000 may not include a reservoir 6200 which, therefore, necessitates touching the application surface 6100 of the stencil 6000 to an ink pad prior to contacting the breast 1000. In yet another alternative embodiment, the application surface 6100 may be preloaded with ink at the time of manufacture of the stencil 6000. A cap or other covering may be used to prevent drying of the ink 6300. In use, the stencil 6000 is pressed against the breast 1000 to transfer the ink and create a line or other marking along which the incision is to be made.

The present invention has been described with reference to the desirable embodiments. Obvious modifications and alterations will occur to others upon reading and understanding the preceding detailed description. It is intended that the invention be construed as including all such modifications and alterations insofaras they come within the scope of the appended claims or the equivalents thereof.

The invention claimed is:

1. A device for establishing an area of incision on a breast, the device comprising:
   a positioning component adapted to be positioned on or adjacent to a nipple areola complex (NAC) of the breast; and
   a template component connected to the positioning component, wherein the template component includes at least one stencil shaped to facilitate a curved incision marking or curved incision on the breast, wherein each stencil is substantially arcuate shaped, and wherein the degree of arc of each successive stencil is decreased the further each successive stencil is situated from the positioning component.

2. The device of claim 1, wherein the degree of arc of each of the stencils is substantially similar and corresponds to the degree of arc of the positioning component.

3. The device of claim 1, wherein the positioning component is substantially circular or substantially semi-circular.

4. The device of claim 3, wherein the substantially circular positioning component is sized to substantially matingly receive the nipple of the NAC.

5. The device of claim 1, further comprising at least one handle attached thereto.

6. A device for establishing an area of incision on a breast, the device comprising:
   a substantially arcuate-shaped member; and
   an elongated member pivotally connected to at one end and extending substantially from a middle portion of the arcuate-shaped member, wherein the device includes means for adjusting the position of the arcuate-shaped member along the length of the elongated member.

7. The device of claim 6, further comprising a positioning component attached to the other end of the elongated member, wherein the positioning component is adapted to be positioned on or adjacent to a nipple areola complex (NAC) of the breast.

8. The device of claim 7, wherein the positioning component is one of:
   substantially circular and sized to substantially matingly receive the nipple of the NAC;
   substantially circular and sized to substantially axially align with the nipple of the NAC; and
   substantially semi-circular and sized to semi-circumferentially abut the periphery of the areola of the NAC.

9. A method for establishing an area of incision on a breast, the method comprising the steps of:
   aligning a positioning component on or adjacent to a nipple areola complex of the breast;
   aligning a stencil with a skin line of the breast, wherein the stencil is connected to the positioning component; and
   forming a curved incision marking or a curved incision on the breast to substantially correspond with the curvature of the skin line of the breast.

10. The method of claim 9, further comprising the step of adjusting the distance of the stencil from the positioning component.

* * * * *